(12) United States Patent
Jahanian

(10) Patent No.: US 12,251,295 B2
(45) Date of Patent: Mar. 18, 2025

(54) DRESSING WITH SPACER FABRIC TO PROMOTE MEDIAL TENSION

(71) Applicant: KCI Manufacturing Unlimited Company, Athlone (IE)

(72) Inventor: Shervin Jahanian, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 0 days.

(21) Appl. No.: 17/781,552

(22) PCT Filed: Dec. 3, 2020

(86) PCT No.: PCT/IB2020/061466
§ 371 (c)(1),
(2) Date: Jun. 1, 2022

(87) PCT Pub. No.: WO2021/111370
PCT Pub. Date: Jun. 10, 2021

(65) Prior Publication Data
US 2023/0000689 A1    Jan. 5, 2023

Related U.S. Application Data

(60) Provisional application No. 62/943,596, filed on Dec. 4, 2019.

(51) Int. Cl.
*A61F 13/05* (2024.01)
*A61F 13/00* (2024.01)
(Continued)

(52) U.S. Cl.
CPC ............ *A61F 13/05* (2024.01); *A61M 1/915* (2021.05); *A61F 2013/00604* (2013.01); *A61F 2013/5113* (2013.01)

(58) Field of Classification Search
CPC ...... A61F 13/00068; A61F 2013/00604; A61F 13/0216; A61M 1/915
See application file for complete search history.

(56) References Cited

U.S. PATENT DOCUMENTS

| 1,355,846 | A | 10/1920 | Rannells |
| 2,547,758 | A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

"Couple." Merriam-Webster.com Dictionary, Merriam-Webster, https://www.merriam-webster.com/dictionary/couple. Accessed Oct. 31, 2023.*

(Continued)

*Primary Examiner* — Rebecca E Eisenberg
*Assistant Examiner* — Matthew Wrubleski

(57) ABSTRACT

A dressing may include a manifold and a spacer fabric. The manifold may have a first side configured to face the tissue site, a second side opposite the first side, a thickness between the first side and the second side, a first portion, and a second portion. The spacer fabric may extend between the first portion and the second portion and may comprise a first layer coupled to the first portion, a second layer coupled to the second portion, and a spacer layer extending between the first layer and the second layer. The first layer and the second layer may be perpendicular to the first side of the manifold. The dressing may be configured to contract more in a first direction than in a second direction, wherein the first direc- (Continued)

tion is perpendicular to an extension direction of the spacer fabric. Other dressings, apparatus, systems, and methods are disclosed.

20 Claims, 13 Drawing Sheets

(51) Int. Cl.
*A61F 13/511* (2006.01)
*A61M 1/00* (2006.01)

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,983,173 A * | 1/1991 | Patience ............... A61F 13/36 |
| | | 604/384 |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Èwall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0064132 A1 * | 4/2004 | Boehringer ......... A61F 13/0206 |
| | | 602/43 |
| 2005/0182347 A1 * | 8/2005 | Bishop ............... A61F 13/0253 |
| | | 602/43 |
| 2006/0122548 A1 * | 6/2006 | Abrams .............. A61F 13/069 |
| | | 602/41 |
| 2008/0167593 A1 * | 7/2008 | Fleischmann ......... A61M 1/964 |
| | | 604/304 |
| 2010/0305535 A1 * | 12/2010 | Leeming ............. A61F 13/069 |
| | | 602/44 |
| 2011/0224630 A1 | 9/2011 | Simmons et al. |
| 2014/0163491 A1 | 6/2014 | Schuessler et al. |
| 2014/0276491 A1 | 9/2014 | Luckemeyer et al. |
| 2014/0309574 A1 * | 10/2014 | Cotton ................ D04B 21/16 |
| | | 602/44 |

(56) References Cited

U.S. PATENT DOCUMENTS

| | | | |
|---|---|---|---|
| 2015/0080788 | A1 | 3/2015 | Blott et al. |
| 2019/0015258 | A1* | 1/2019 | Gowans ................ A61M 1/90 |

FOREIGN PATENT DOCUMENTS

| | | | | |
|---|---|---|---|---|
| AU | 755496 | B2 | 12/2002 | |
| AU | 2018293064 | A1 * | 12/2019 | ....... A61F 13/00017 |
| CA | 2005436 | A1 | 6/1990 | |
| DE | 26 40 413 | A1 | 3/1978 | |
| DE | 43 06 478 | A1 | 9/1994 | |
| DE | 29 504 378 | U1 | 9/1995 | |
| EP | 0100148 | A1 | 2/1984 | |
| EP | 0117632 | A2 | 9/1984 | |
| EP | 0161865 | A2 | 11/1985 | |
| EP | 0358302 | A2 | 3/1990 | |
| EP | 1018967 | A1 | 7/2000 | |
| GB | 692578 | A | 6/1953 | |
| GB | 2195255 | A | 4/1988 | |
| GB | 2 197 789 | A | 6/1988 | |
| GB | 2 220 357 | A | 1/1990 | |
| GB | 2 235 877 | A | 3/1991 | |
| GB | 2 329 127 | A | 3/1999 | |
| GB | 2 333 965 | A | 8/1999 | |
| GB | 2468905 | A | 9/2010 | |
| JP | 2007548686 | | * 3/2007 | |
| JP | 4129536 | B2 | 8/2008 | |
| SG | 71559 | | 4/2002 | |
| WO | 80/02182 | A1 | 10/1980 | |
| WO | 87/04626 | A1 | 8/1987 | |
| WO | 90/010424 | A1 | 9/1990 | |
| WO | 93/009727 | A1 | 5/1993 | |
| WO | 94/20041 | A1 | 9/1994 | |
| WO | 96/05873 | A1 | 2/1996 | |
| WO | 97/18007 | A1 | 5/1997 | |
| WO | 99/13793 | A1 | 3/1999 | |
| WO | 2009/071894 | A1 | 6/2009 | |
| WO | 2019/002085 | A1 | 1/2019 | |

OTHER PUBLICATIONS

"Join." Merriam-Webster.com Dictionary, Merriam-Webster, https://www.merriam-webster.com/dictionary/join. Accessed Oct. 31, 2023.*

International Search Report and Written Opinion Corresponding to Application No. PCT/IB2020/061466, mailed Mar. 5, 2021.

Louis C. Argenta, Md and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, Md et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp.: 1-5.

Kostyuchenok, B.M., et al.; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp.: 66-70, and 9 page English translation thereof.

Yusupov. Yu.N., et al.; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp.: 48-52, and 8 page English translation thereof.

Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp.: 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp.: 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

(56) References Cited

OTHER PUBLICATIONS

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

\* cited by examiner

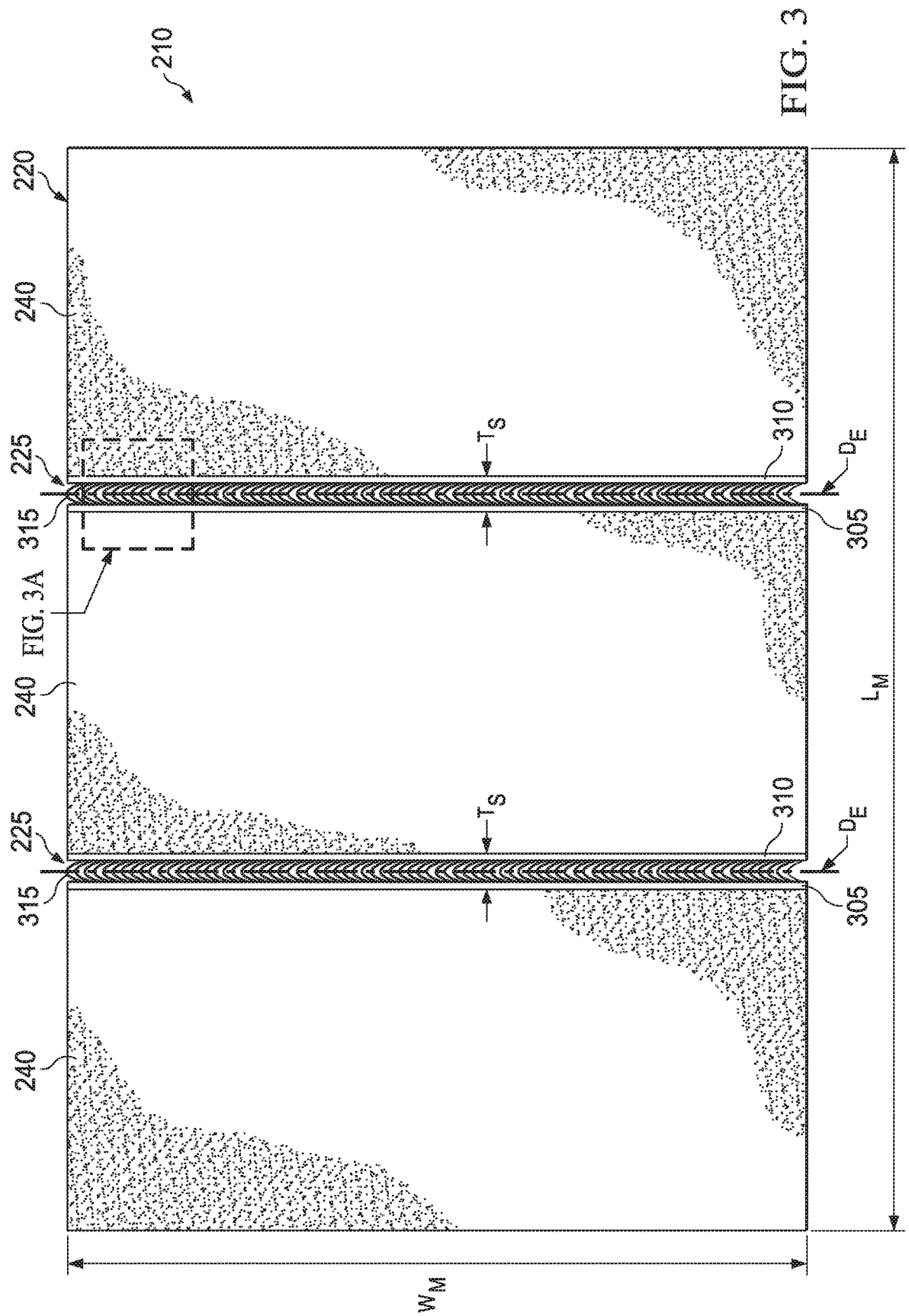

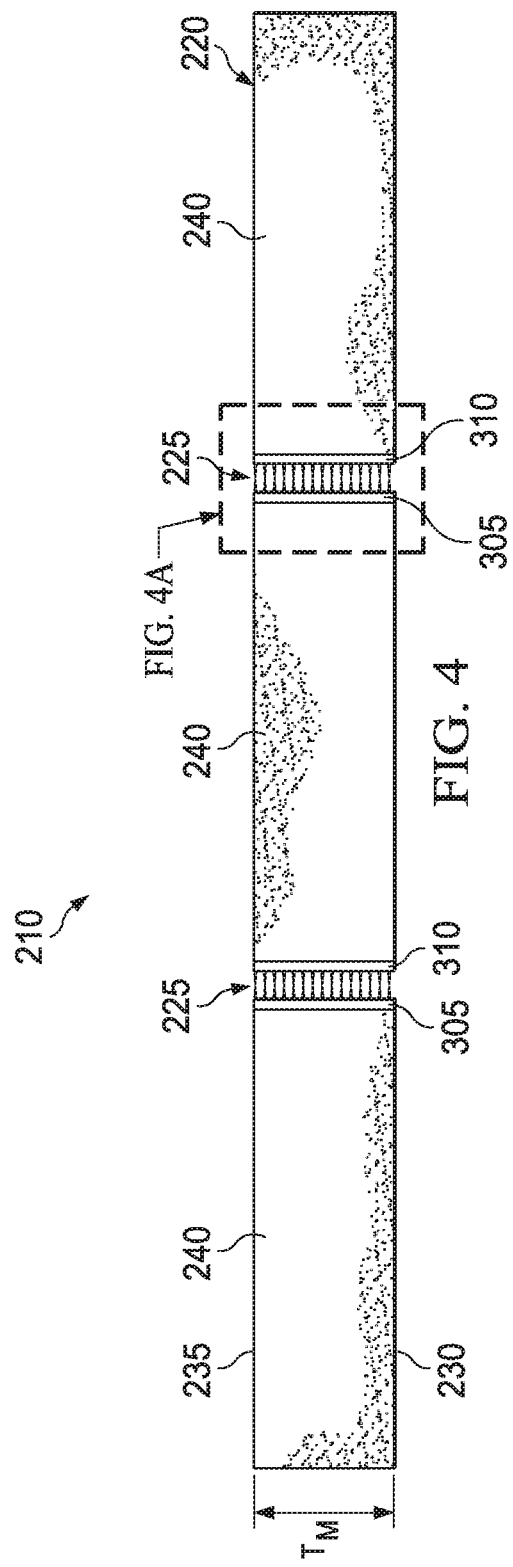

DRESSING WITH SPACER FABRIC TO PROMOTE MEDIAL TENSION

CROSS-REFERENCE TO RELATED APPLICATIONS

This application claims the benefit of priority to U.S. Provisional Application No. 62/943,596, filed on Dec. 4, 2019, which is incorporated herein by reference in its entirety.

TECHNICAL FIELD

The invention set forth in the appended claims relates generally to tissue treatment systems and more particularly, but without limitation, to dressings for tissue treatment and methods of using the dressings for tissue treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a dressing for treating tissue may be a composite of dressing layers, including a contact layer, a manifold layer, and an adhesive drape. The contact layer may include a perforated polymer film in some embodiments. The manifold layer may include a manifold having one or more of strips of spacer fabric in or coupled to the manifold in some examples. The manifold may include an open-cell foam in some examples. The one or more strips of spacer fabric may be inlaid partially or fully transverse in the manifold. In some examples, the one or more strips of spacer fabric may extend parallel across the manifold. In other examples, the one or more strips of spacer fabric may extend in one or more angles across the manifold. The strips of spacer fabric may allow for controlled contraction of the dressing in a manner that is tunable. In some embodiments, the dressing may be coupled to the patient such that the strips of spacer fabric may be oriented parallel to a tissue site, such as a linear wound. A negative pressure may be applied to the manifold layer and the strips of spacer fabric may promote medial or lateral contraction of the dressing to pull the linear wound closed. The lateral contraction of the dressing provided by the strips of spacer fabric may be propagated to tissue underlying the linear wound, reducing the chance of dehiscence and drawing the wound or edges of an incision together. Embodiments of the dressing may allow for a reduction in healing complications and promote healing of the tissue site. In some embodiments, the strips of spacer fabric may allow for preferential contraction in certain areas of the dressing to allow the dressing to conform around specific geometries or anatomies.

More generally, some embodiments of a dressing may include a manifold and a spacer fabric. The manifold may have a first side configured to face the tissue site, a second side opposite the first side, a thickness between the first side and the second side, a first portion, and a second portion. The spacer fabric may extend between the first portion and the second portion and may comprise a first layer coupled to the first portion, a second layer coupled to the second portion, and a spacer layer extending between the first layer and the second layer. The first layer and the second layer may be perpendicular to the first side of the manifold.

Some embodiments of a dressing may include a manifold having a first side configured to face a tissue site, a second side opposite the first side, and a thickness between the first side and the second side. The dressing may further include a channel extending into the manifold on the second side and having a depth measured from the second side. A spacer fabric may be disposed in the channel, wherein the spacer fabric may comprise a first layer, a second layer, and a spacer layer extending between the first layer and the second layer. The first layer and the second layer may be perpendicular to the first side of the manifold.

Other embodiments of a dressing for treating a tissue site with negative pressure may include a tissue interface comprising two or more strips of spacer fabric and a manifold between each strip of spacer fabric. In some embodiments, the two or more strips of spacer fabric may be at an angle relative to one another. In some embodiments, the two or more strips of spacer fabric may be configured to bias against contraction of the manifold parallel to the strips of spacer fabric.

Yet other embodiments of a dressing for use in treating a tissue site with negative pressure may comprise a manifold and a connective structure. The manifold may have a first side configured to face the tissue site, a second side opposite the first side, a thickness between the first side and the second side, a first portion, and a second portion. The connective structure may be coupled to the first portion and the second portion and may extend in an extension direction across the manifold. The dressing may be configured to anisotropically contract such that the dressing may be configured to contract more in a first direction than in a second direction, wherein the first direction is perpendicular to the extension direction of the connective structure.

A system for treating a tissue site with negative pressure is also described herein, wherein some embodiments of the system may comprise a dressing, a fluid conductor configured to be fluidly coupled to the dressing, and a negative-pressure source configured to be fluidly coupled to the fluid conductor. The dressing may comprise a manifold, a spacer fabric, and a cover. The manifold may have a first side configured to face the tissue site, a second side opposite the first side, a thickness between the first side and the second side, a first portion, and a second portion. The spacer fabric may extend between the first portion and the second portion and may comprise a first layer coupled to the first portion, a second layer coupled to the second portion, and a spacer layer extending between the first layer and the second layer. The first layer and the second layer may be perpendicular to the first side of the manifold. The cover may be configured to be disposed over the manifold and the spacer fabric.

A method for treating a tissue site with negative pressure is also described herein, wherein some example embodiments include applying a tissue interface to the tissue site, covering the tissue interface with a cover to form a sealed space containing the tissue interface, fluidly coupling a fluid conductor to the tissue interface, fluidly coupling the fluid conductor to a negative-pressure source, and applying negative pressure from the negative-pressure source to the tissue interface through fluid conductor. The tissue interface may comprise a manifold and a spacer fabric. The manifold may have a first side configured to face the tissue site, a second side opposite the first side, a thickness between the first side and the second side, a first portion, and a second portion. The spacer fabric may extend between the first portion and the second portion and may comprise a first layer coupled to the first portion, a second layer coupled to the second portion, and a spacer layer extending between the first layer and the second layer. The first layer and the second layer may be perpendicular to the first side of the manifold. The method may further comprise contracting the tissue interface in response to an application of negative pressure to the tissue interface, wherein the tissue interface is configured to anisotropically contract such that the tissue interface is configured to contract more in a first direction than in a second direction, wherein the first direction is perpendicular to an extension direction of the spacer fabric.

Other objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 3 is a top view of an example layer that can be associated with some embodiments of the tissue interface of FIG. 2;

FIG. 4 is a side view of the layer of FIG. 3;

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

Figure 1:
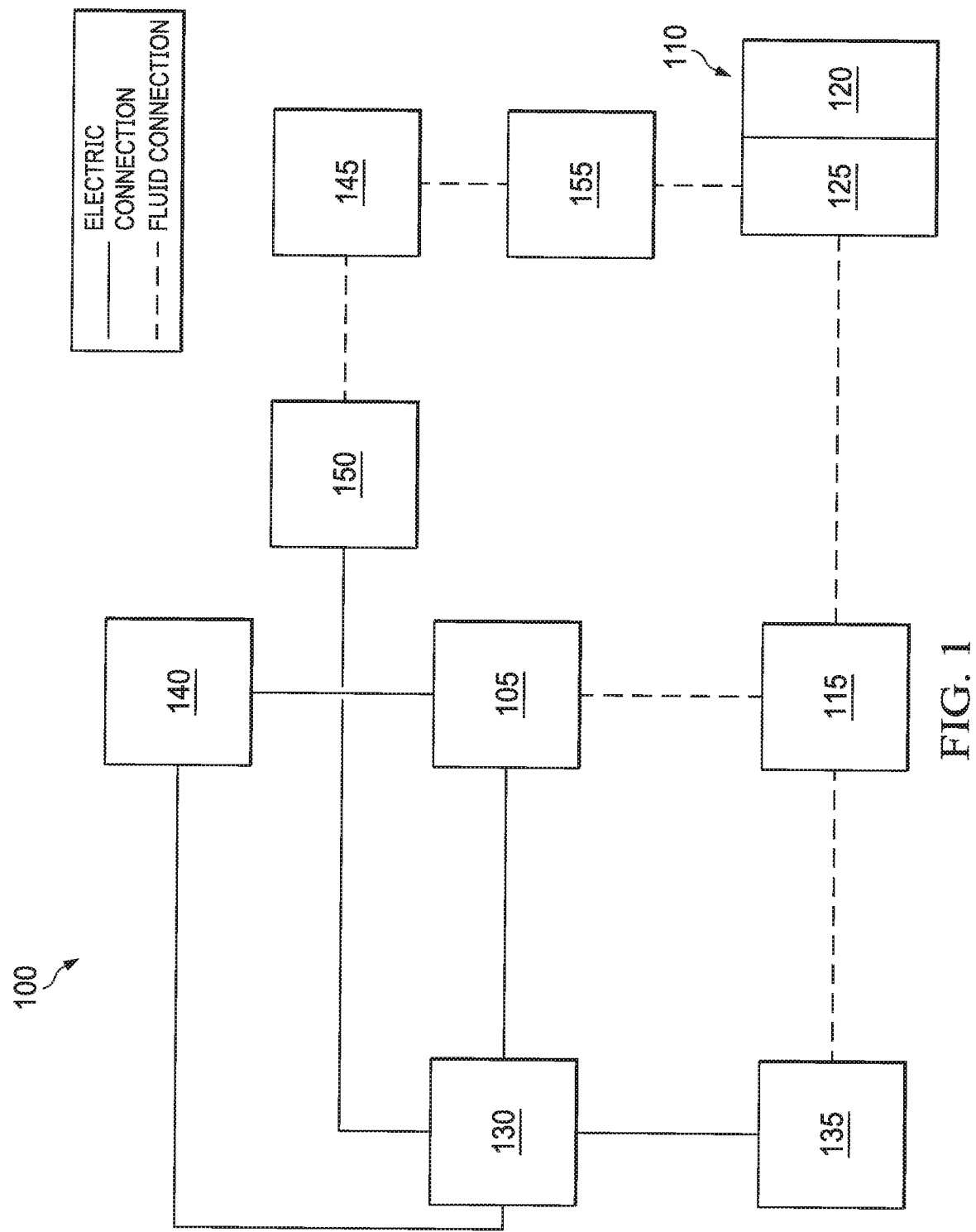
FIG. 1 is a block diagram of an example embodiment of a therapy system that can provide negative-pressure treatment and instillation treatment in accordance with this specification.

FIG. 1 is a block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on a body that is exposed to the external environment, such as an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source, such as a positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polyamide copolymers. Such materials are commercially available as, for example, Tegaderm® drape, commercially available from 3M Company, Minneapolis Minnesota; polyurethane (PU) drape; polyether block polyamide copolymer (PEBAX), for example; and INSPIRE 2301 and INSPIRE 2327 polyurethane films, commercially available from Expopack Advanced Coatings, Wrexham, United Kingdom. In some embodiments, the cover 125 may comprise INSPIRE 2301 having an MVTR (upright cup technique) of 2600 $g/m^2/24$ hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" may refer to a location in a fluid path relatively closer to a source of negative pressure or further away from a source of positive pressure. Conversely, the term "upstream" may refer to a location further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

In some embodiments, the controller 130 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 130 can operate the negative-pressure source 105 to cycle between a target pressure and atmospheric pressure. For example, the target pressure may be set at a value of 135 mmHg for a specified period of time (e.g., 5 min), followed by a specified period of time (e.g., 2 min) of deactivation. The cycle can be repeated by activating the negative-pressure source 105, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time. The initial rise time may vary depending on the type of dressing and therapy equipment being used. For example, some therapy systems may increase negative pressure at a rate of about 20-30 mmHg/second, and other therapy systems may increase negative pressure at a rate of about 5-10 mmHg/second. If the therapy system 100 is operating in an intermittent mode, the repeating rise time may be a value substantially equal to the initial rise time.

In some example dynamic pressure control modes, the target pressure can vary with time. For example, the target pressure may vary in the form of a triangular waveform, varying between a negative pressure of 50 and 135 mmHg with a rise rate of negative pressure set at a rate of 25 mmHg/min. and a descent rate set at 25 mmHg/min. In other embodiments of the therapy system 100, the triangular waveform may vary between negative pressure of 25 and 135 mmHg with a rise rate of about 30 mmHg/min and a descent rate set at about 30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

In some embodiments, the controller 130 may receive and process data, such as data related to instillation solution provided to the tissue interface 120. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second to 30 minutes. The controller 130 may also control the operation of one or more components of the therapy system 100 to instill solution. For example, the controller 130 may manage fluid distributed from the solution source 145 to the tissue interface 120. In some embodiments, fluid may be instilled to a tissue site by applying a negative pressure from the negative-pressure source 105 to reduce the pressure at the tissue site, drawing solution into the tissue interface 120. In some embodiments, solution may be instilled to a tissue site by applying a positive pressure from the positive-pressure source 150 to move solution from the solution source 145 to the tissue interface 120. Additionally or alternatively, the solution source 145 may be elevated to a height sufficient to allow gravity to move solution into the tissue interface 120.

The controller 130 may also control the fluid dynamics of instillation by providing a continuous flow of solution or an intermittent flow of solution. Negative pressure may be applied to provide either continuous flow or intermittent flow of solution. The application of negative pressure may be implemented to provide a continuous pressure mode of operation to achieve a continuous flow rate of instillation solution through the tissue interface 120, or it may be implemented to provide a dynamic pressure mode of operation to vary the flow rate of instillation solution through the tissue interface 120. Alternatively, the application of negative pressure may be implemented to provide an intermittent mode of operation to allow instillation solution to dwell at the tissue interface 120. In an intermittent mode, a specific fill volume and dwell time may be provided depending, for example, on the type of tissue site being treated and the type of dressing being utilized. After or during instillation of solution, negative-pressure treatment may be applied. The controller 130 may be utilized to select a mode of operation and the duration of the negative pressure treatment before commencing another instillation cycle.

Figure 2:
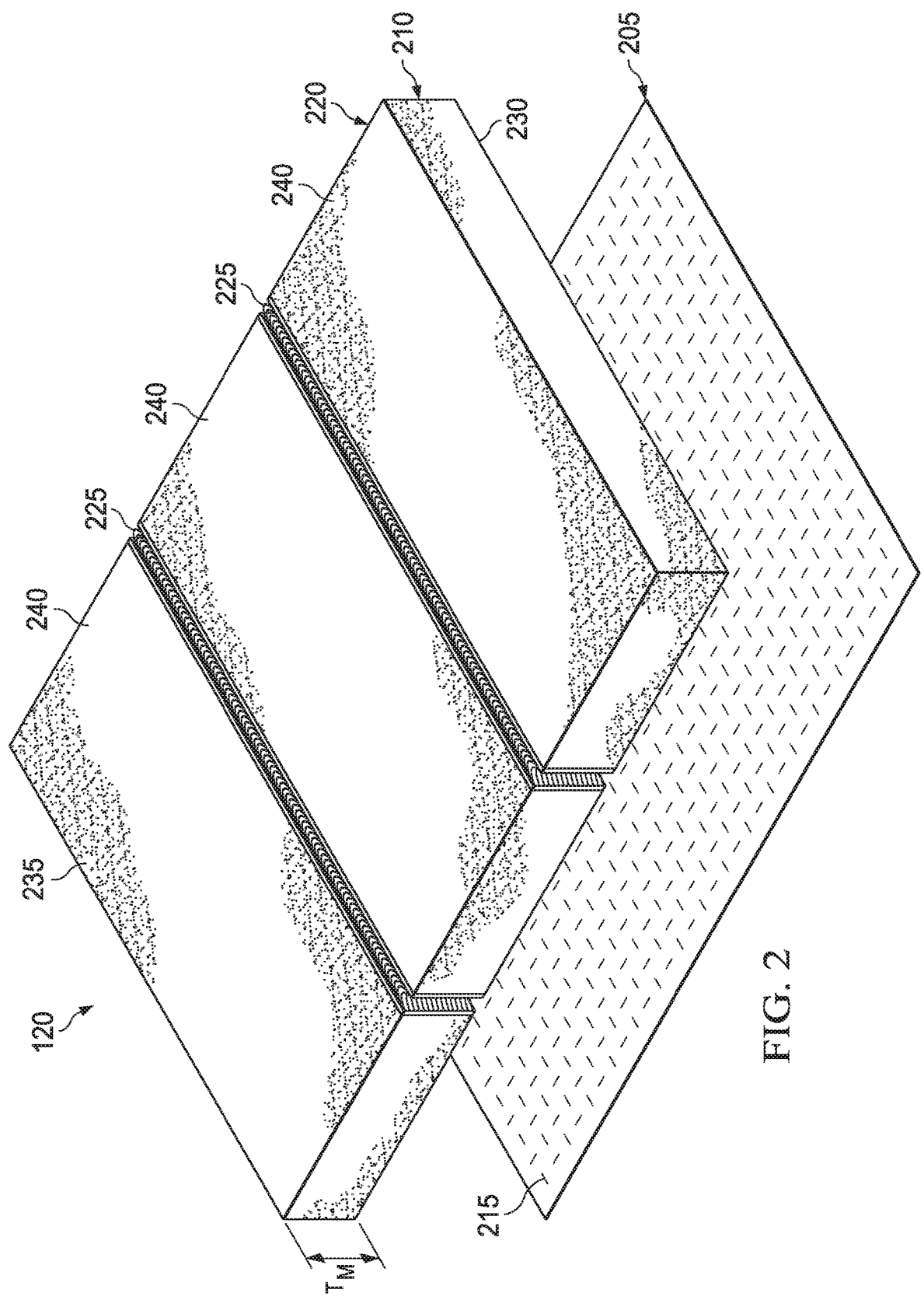
FIG. 2 is an exploded view of an example of a tissue interface that can be associated with some embodiments of the therapy system of FIG. 1.

FIG. 2 is an exploded view of an example of the tissue interface 120 of FIG. 1, illustrating additional details that may be associated with some embodiments in which the tissue interface 120 comprises more than one layer. In the example of FIG. 2, the tissue interface comprises a first layer, such as a contact layer 205, and a second layer, such as a manifold layer 210. In some embodiments, the contact layer 205 may be disposed adjacent to the manifold layer 210. For example, the contact layer 205 and the manifold layer 210 may be stacked so that the contact layer 205 is in contact with the manifold layer 210. The contact layer 205 may also be heat-bonded or adhered to the manifold layer 210 in some embodiments. In some embodiments, the contact layer 205 optionally includes a low-tack adhesive, which can be configured to hold the tissue interface 120 in place while the cover 125 is applied. The low-tack adhesive may be continuously coated on the contact layer 205 or applied in a pattern.

The contact layer 205 may comprise or consist essentially of a means for controlling or managing fluid flow. In some embodiments, the contact layer 205 may be a fluid control layer comprising or consisting essentially of a liquid-impermeable, elastomeric material. For example, the contact layer 205 may comprise or consist essentially of a polymer film, such as a polyurethane film. In some embodiments, the contact layer 205 may comprise or consist essentially of the same material as the cover 125. The contact layer 205 may also have a smooth or matte surface texture in some embodiments. A glossy or shiny finish finer or equal to a grade B3 according to the SPI (Society of the Plastics Industry) standards may be particularly advantageous for some applications. In some embodiments, variations in surface height may be limited to acceptable tolerances. For example, the surface of the contact layer 205 may have a substantially flat surface, with height variations limited to 0.2 millimeters over a centimeter.

In some embodiments, the contact layer 205 may be hydrophobic. The hydrophobicity of the contact layer 205 may vary, but may have a contact angle with water of at least ninety degrees in some embodiments. In some embodiments the contact layer 205 may have a contact angle with water of no more than 150 degrees. For example, in some embodiments, the contact angle of the contact layer 205 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, VA, and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles herein represent averages of 5-9 measured values, discarding both the highest and lowest measured values. The hydrophobicity of the contact layer 205 may be further enhanced with a hydrophobic coating of other materials, such as silicones and fluorocarbons, either as coated from a liquid, or plasma coated.

The contact layer 205 may also be suitable for welding to other layers, including the manifold layer 210. For example, the contact layer 205 may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene.

The area density of the contact layer 205 may vary according to a prescribed therapy or application. In some embodiments, an area density of less than 40 grams per square meter may be suitable, and an area density of about 20-30 grams per square meter may be particularly advantageous for some applications.

In some embodiments, for example, the contact layer 205 may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styrenics, silicones, fluoropolymers, and acetates. A thickness between 20 microns and 100 microns may be suitable for many applications. Films may be clear, colored, or printed. More polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

The contact layer 205 may have one or more passages, which can be distributed uniformly or randomly across the contact layer 205. The passages may be bi-directional and pressure-responsive. For example, each of the passages generally may comprise or consist essentially of an elastic passage that is normally unstrained to substantially reduce liquid flow, and can expand or open in response to a pressure gradient. As illustrated in the example of FIG. 2, the passages may comprise or consist essentially of perforations 215 in the contact layer 205. Perforations 215 may be formed by removing material from the contact layer 205. For example, perforations 215 may be formed by cutting through the contact layer 205. In the absence of a pressure gradient across the perforations 215, the perforations 215 may be sufficiently small to form a seal or fluid restriction, which can substantially reduce or prevent liquid flow. Additionally, or alternatively, one or more of the passages may be or may function as an elastomeric valve that is normally closed when unstrained to substantially prevent liquid flow, and can open in response to a pressure gradient. In some examples, the passages may comprise or consist essentially of fenestrations in the contact layer 205. Generally, fenestrations are a species of perforation, and may also be formed by removing material from the contact layer 205. The amount of material removed and the resulting dimensions of the fenestrations may be up to an order of magnitude less than perforations.

In some embodiments, the perforations 215 may be formed as slots (or fenestrations formed as slits) in the contact layer 205. In some examples, the perforations 215 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeter may also be acceptable. Such dimensions and tolerances may be achieved with a laser cutter, for example. Slots of such configurations may function as imperfect elastomeric valves that can substantially reduce liquid flow in a normally closed or resting state. For example, such slots may form a flow restriction without being completely closed or sealed. The slots can expand or open wider in response to a pressure gradient to allow increased liquid flow.

The manifold layer 210 generally comprises or consists essentially of a manifold 220 and one or more strips of spacer fabric 225 coupled to the manifold 220. The manifold 220 can provide a means for collecting or distributing fluid across the tissue interface 120 under pressure. For example, the manifold 220 may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as from a source of instillation solution, across the tissue interface 120.

In some illustrative embodiments, the pathways of the manifold 220 may be interconnected to improve distribution or collection of fluids. In some illustrative embodiments, the manifold 220 may comprise or consist essentially of a porous material having interconnected fluid pathways. Examples of suitable porous material that comprise or can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, the manifold 220 may additionally or alternatively comprise projections that form interconnected fluid pathways. For example, the manifold 220 may be molded to provide surface projections that define interconnected fluid pathways.

In some embodiments, the manifold 220 may comprise or consist essentially of a reticulated foam having pore sizes and free volume that may vary according to needs of a prescribed therapy. For example, a reticulated foam having a free volume of at least 90% may be suitable for many therapy applications, and a foam having an average pore size in a range of 400-600 microns may be particularly suitable for some types of therapy. The tensile strength of the manifold 220 may also vary according to needs of a prescribed therapy. For example, the tensile strength of a foam may be increased for instillation of topical treatment solutions. The 25% compression load deflection of the manifold 220 may be at least 0.35 pounds per square inch, and the 65% compression load deflection may be at least 0.43 pounds per square inch. In some embodiments, the tensile strength of the manifold 220 may be at least 10 pounds per square inch. The manifold 220 may have a tear strength of at least 2.5 pounds per inch. In some embodiments, the manifold 220 may be a foam comprised of polyols such as polyester or polyether, isocyanate such as toluene diisocyanate, and polymerization modifiers such as amines and tin compounds. In some examples, the manifold layer 210 may be a reticulated polyurethane foam such as used in GRANUFOAM™ dressing or V.A.C. VERAFLO™ dressing, both available from KCI of San Antonio, Texas.

As further shown in FIG. 2, the manifold 220 includes a first side 230 configured to face a tissue site, a second side 235 opposite the first side 230, and a thickness $T_M$ between the first side 230 and the second side 235. In some embodiments, the manifold 220 may comprise one or more manifold portions 240. In some embodiments, the manifold portions 240 may be connected to one another. In other embodiments, the manifold portions 240 may be discontinuous.

Figure 3A:
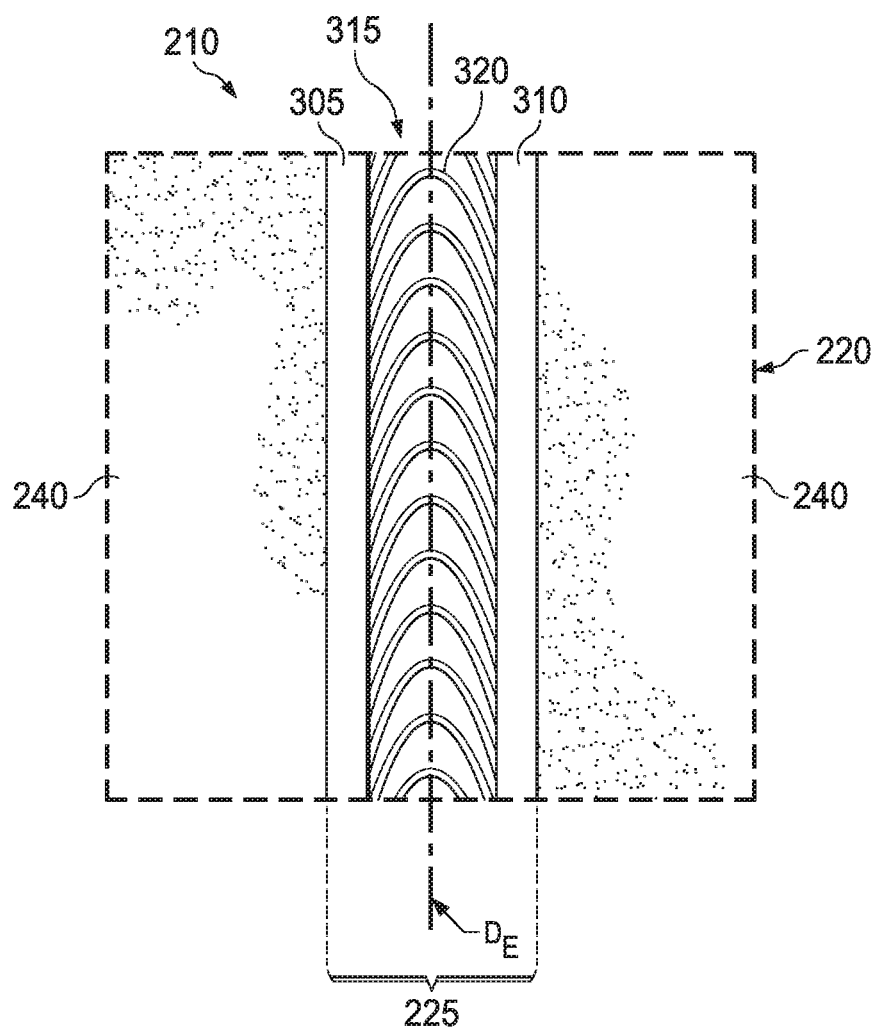
FIG. 3A is a top detail view taken at reference FIG. 3A of FIG. 3.

FIG. 3 and FIG. 3A illustrate an example of the manifold layer 210 that can be associated with some embodiments of the tissue interface 120 of FIG. 2. FIG. 3 is a top view of the manifold layer 210. FIG. 3A is a top detail view of the manifold layer 210 of FIG. 3. As shown in FIG. 3, the manifold 220 may have a length $L_M$ and a width $W_M$. The strips of spacer fabric 225 may extend across the manifold 220 in an extension direction $D_E$. In some embodiments, the extension direction $D_E$ of the strips of spacer fabric 225 may be parallel to the width $W_M$ of the manifold 220. In some embodiments, extension direction $D_E$ of the strips of spacer fabric 225 may be at an angle with respect to the width $W_M$ of the manifold 220. As shown in the example of FIG. 3, in some embodiments, the strips of spacer fabric 225 may be parallel to one another and may be parallel to the width $W_M$ of the manifold 220. In some embodiments, the strips of spacer fabric 225 may be parallel to one another and may be at an angle with respect to the width $W_M$ of the manifold 220.

Each strip of spacer fabric 225 may comprise a first layer 305, a second layer 310, and a spacer layer 315 extending between the first layer 305 and the second layer 310. Each strip of spacer fabric 225 may have a thickness $T_S$ from the first layer 305 to the second layer 310. The first layer 305 may comprise a first fabric and the second layer 310 may comprise a second fabric. For example, the first layer 305 and the second layer 310 may each comprise a knit fabric. In some embodiments, the first layer 305 and the second layer 310 may each comprise a woven fabric. For example, the first layer 305 and the second layer 310 may each comprise a warp knitted fabric using one or more yarns. In some embodiments, the first layer 305 and the second layer 310 may comprise polyester yarn.

The first layer 305 and the second layer 310 may comprise multifilament yarns. For example, in some embodiments, the multifilament yarns used to form the first layer 305 and the second layer 310 may have about 30 to about 150 filaments. In some embodiments, the multifilament yarns used to form the first layer 305 and the second layer 310 may have about 50 to about 150 filaments. In some embodiments, the multifilament yarns used to form the first layer 305 and the second layer 310 may have about 36 filaments. In some embodiments, the multifilament yarns used to form the first layer 305 and the second layer 310 may have about 48 filaments. In some embodiments, the multifilament yarns used to form the first layer 305 and the second layer 310 may have about 100 filaments. In some embodiments, the multifilament yarns used to form the first layer 305 and the second layer 310 may have about 138 filaments.

In some embodiments, the multifilament yarns used to form the first layer 305 and the second layer 310 may have a denier per filament of about 1 to about 6. In some embodiments, the multifilament yarns used to form the first layer 305 and the second layer 310 may have a denier per filament of about 1.5. In some embodiments, the multifilament yarns used to form the first layer 305 and the second layer 310 may have a denier per filament of about 2.4. In some embodiments, the multifilament yarns used to form the first layer 305 and the second layer 310 may have a denier per filament of about 3.4. In some embodiments, the multifilament yarns used to form the first layer 305 and the second layer 310 may have a denier per filament of about 5.5.

The first layer 305 and the second layer 310 may each have a thickness of about 0.10 inches to about 0.30 inches. In some embodiments, the first layer 305 and the second layer 310 may each have a thickness of about 0.12 inches. In some embodiments, the first layer 305 and the second layer 310 may each have a thickness of about 0.15 inches. In some embodiments, the first layer 305 and the second layer 310 may each have a thickness of about 0.17 inches. In some embodiments, the first layer 305 and the second layer 310 may each have a thickness of about 0.25 inches.

The first layer 305 and the second layer 310 may each have a weight per unit area of about 5.0 ounces/yard$^2$ to about 25.0 ounces/yard$^2$. In some embodiments, the first layer 305 and the second layer 310 may each have a weight per unit area of about 8.4 ounces/yard$^2$. In some embodiments, the first layer 305 and the second layer 310 may each have a weight per unit area of about 10.2 ounces/yard$^2$. In some embodiments, the first layer 305 and the second layer 310 may each have a weight per unit area of about 12.5 ounces/yard$^2$. In some embodiments, the first layer 305 and the second layer 310 may each have a weight per unit area of about 22.8 ounces/yard$^2$.

As shown in the example of FIG. 3A, the spacer layer 315 may comprise one or more pile yarns 320 extending between the first layer 305 and the second layer 310. The pile yarns 320 may be interknitted with the first layer 305 and the second layer 310. The first layer 305 and the second layer 310 may be integrated with one another by the pile yarns 320. In some embodiments, the first layer 305 and the second layer 310 may be connected by a single pile yarn 320. In some embodiments, each pile yarn 320 comprises monofilament yarn. In some embodiments, the pile yarn 320 may comprise polyester yarn. In some embodiments, the pile yarn 320 may have a denier per filament of about 30 to about 250. In some embodiments, the pile yarn 320 may have a denier per filament of about 32.9. In some embodiments, the pile yarn 320 may have a denier per filament of about 37.7. In some embodiments, the pile yarn 320 may have a denier per filament of about 107.9. In some embodiments, the pile yarn 320 may have a denier per filament of about 209.1.

In some embodiments, the first layer 305 and the second layer 310 may comprise multifilament polyester yarn having 138 filaments with a denier per filament of 1.5 and the pile yarn 320 may comprise a monofilament polyester yarn having a denier per filament of 37.7. In some embodiments, the first layer 305 and the second layer 310 may comprise multifilament polyester yarn having 100 filaments with a denier per filament of 3.4 and the pile yarn 320 may comprise a monofilament polyester yarn having a denier per filament of 209.1. In some embodiments, the first layer 305 and the second layer 310 may comprise multifilament polyester yarn having 36 filaments with a denier per filament of 2.4 and the pile yarn 320 may comprise a monofilament polyester yarn having a denier per filament of 32.9. In some embodiments, the first layer 305 and the second layer 310 may comprise multifilament polyester yarn having 48 filaments with a denier per filament of 5.5 and the pile yarn 320 may comprise a monofilament polyester yarn having a denier per filament of 107.9.

The one or more strips of spacer fabric 225 may be connective structures that couple the manifold portions 240 together. There may be a manifold portion 240 between each strip of spacer fabric 225. The first layer 305 and the second layer 310 of each strip of spacer fabric 225 may be coupled to the manifold 220 in a variety of ways. For example, in some embodiments, the first layer 305 and the second layer 310 may be coupled to the manifold 220 with glue. In some embodiments, the first layer 305 and the second layer 310 may be coupled to the manifold 220 using a hot melt adhesive. In some embodiments, the first layer 305 and the second layer 310 may be welded to the manifold 220 using heat, radio frequency (RF) welding, or other methods to generate heat such as ultrasonic welding.

Figure 4A:
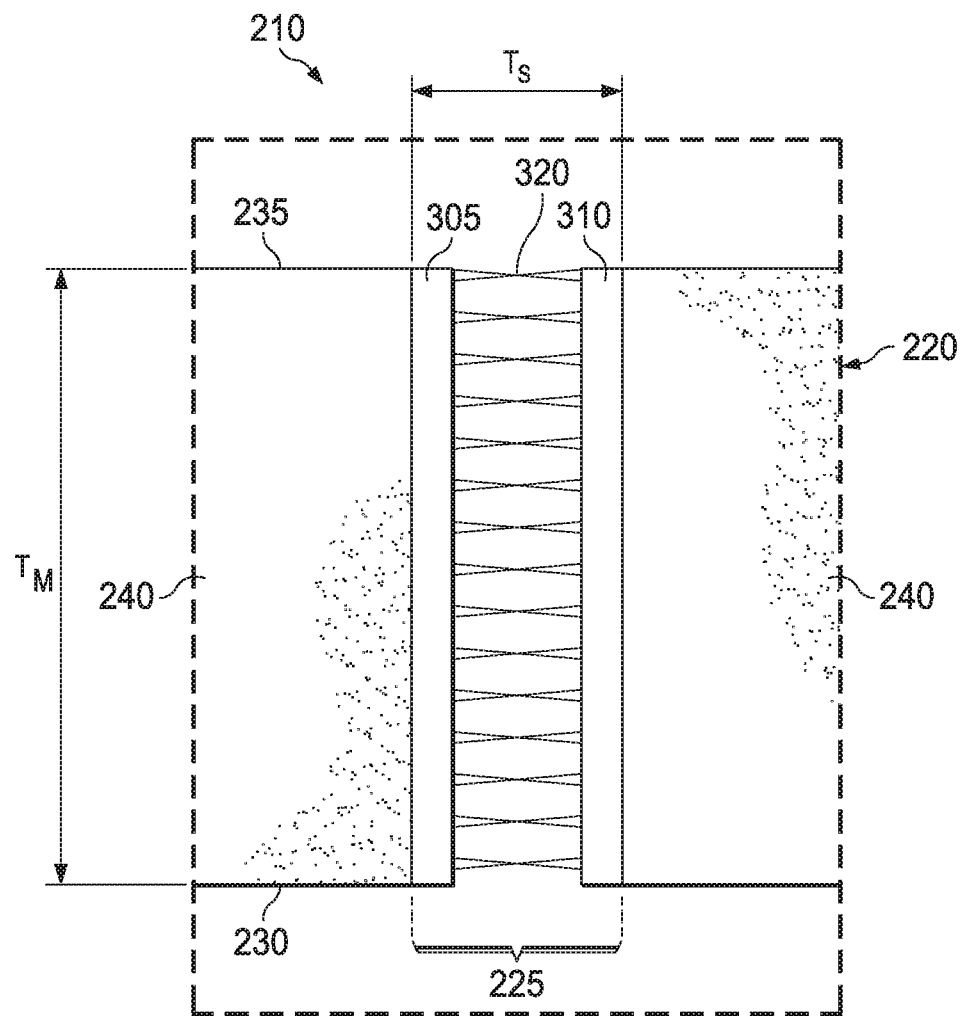
FIG. 4A is a side detail view taken at reference FIG. 4A in FIG. 4.

FIG. 4 is a side view of the manifold layer 210 of FIG. 3. FIG. 4A is a detail view of the manifold layer 210 of FIG. 3. As illustrated in FIG. 4 and FIG. 4A, in some embodiments, the first layer 305 and the second layer 310 of each strip of spacer fabric 225 may be oriented perpendicular to the first side 230 and the second side 235 of the manifold 220. The first layer 305 may form a first side of the strip of spacer fabric 225 and the second layer 310 may form a second side of the strip of spacer fabric 225. The first side of each strip of spacer fabric 225 may be positioned perpendicular to the first side 230 and the second side 235 of the manifold 220. The second side of each strip of spacer fabric 225 may be positioned perpendicular to the first side 230 and the second side 235 of the manifold 220. The first layer 305 and the second layer 310 of each strip of spacer fabric 225 may be positioned in a plane parallel to the thickness $T_M$ of the manifold 220. The spacer layer 315 may maintain the first layer 305 and the second layer 310 in a spaced-apart parallel relation. As shown in FIG. 4A, the thickness $T_S$ of each strip of spacer fabric 225 may be perpendicular to the thickness $T_M$ of the manifold 220.

Referring again to FIG. 3, in some embodiments, the one or more strips of spacer fabric 225 may function as a manifold, for example, the spacer fabric 225 may be adapted to receive negative pressure from a source and distribute negative pressure through and/or between the first layer 305, the second layer 310, and the pile yarns 320. In some embodiments, if the manifold layer 210 is subjected to negative pressure, fluid may be removed from between the first layer 305 and the second layer 310 of each spacer fabric 225, drawing the first layer 305 and the second layer 310 toward one another, and reducing the thickness $T_S$ between the first layer 305 and the second layer 310. Any manifold portions 240 coupled to the strips of spacer fabric 225 are likewise configured to be drawn toward one another if the manifold layer 210 is subjected to negative pressure. In some embodiments, the each of the strips of spacer fabric 225 may be more rigid along the extension direction $D_E$ than in a direction perpendicular to the extension direction $D_E$, the first layer 305, and the second layer 310. The strips of spacer fabric 225 may be configured to resist contraction parallel to the extension direction $D_E$ and may direct contraction perpendicular to the extension direction $D_E$. If a manifold is subjected to negative pressure, it may tend to collapse or contract in all directions. The one or more strips of spacer fabric 225 may provide anisotropic properties to the manifold layer 210. In some embodiments, the manifold layer 210 may be configured to anisotropically contract such that the manifold layer 210 contracts more in a first direction than in a second direction, wherein the first direction is perpendicular to the extension direction $D_E$ of the strip of spacer fabric 225. As shown in the example of FIG. 3, wherein the extension direction $D_E$ of the strip of spacer fabric 225 is parallel to the width $W_M$ of the manifold 220, the strip of spacer fabric 225 may be configured to bias against contraction of the manifold 220 parallel to the width $W_M$ of the manifold 220 and the strip of spacer fabric 225 may be configured to direct contraction of the manifold perpendicular to the width $W_M$ of the manifold 220. The one or more strips of spacer fabric 225 may cause greater contraction along the length $L_M$ of the manifold 220 than along the width $W_M$ of the manifold 220.

The properties of the one or more strips of spacer fabric 225 may be selected to tune the performance of the manifold layer 210 as desired for a particular therapy. For example, the anisotropic properties of the manifold layer 210 can be increased or decreased by modifying one or more of the thickness of the first layer 305 and the second layer 310, the thickness $T_S$ between the first layer 305 and the second layer 310, and the filament material, the number of filaments, the weight of the filaments, and the denier per filament used to manufacture the first layer 305, the second layer 310, and the pile yarn 320.

Figure 5:
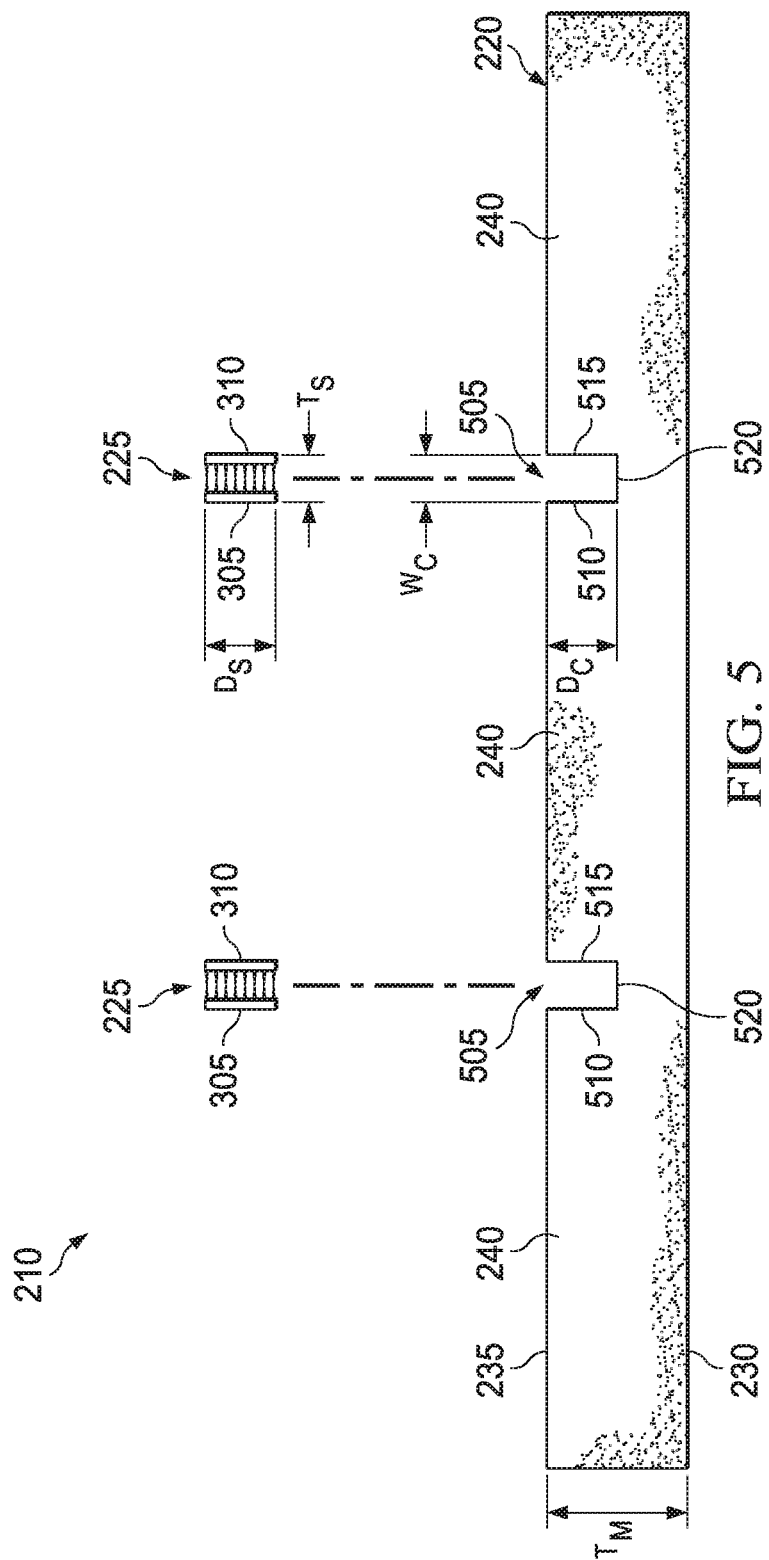
FIG. 5 is an exploded view of another example layer that can be associated with some embodiments of the tissue interface of FIG. 2.
Figure 5A:
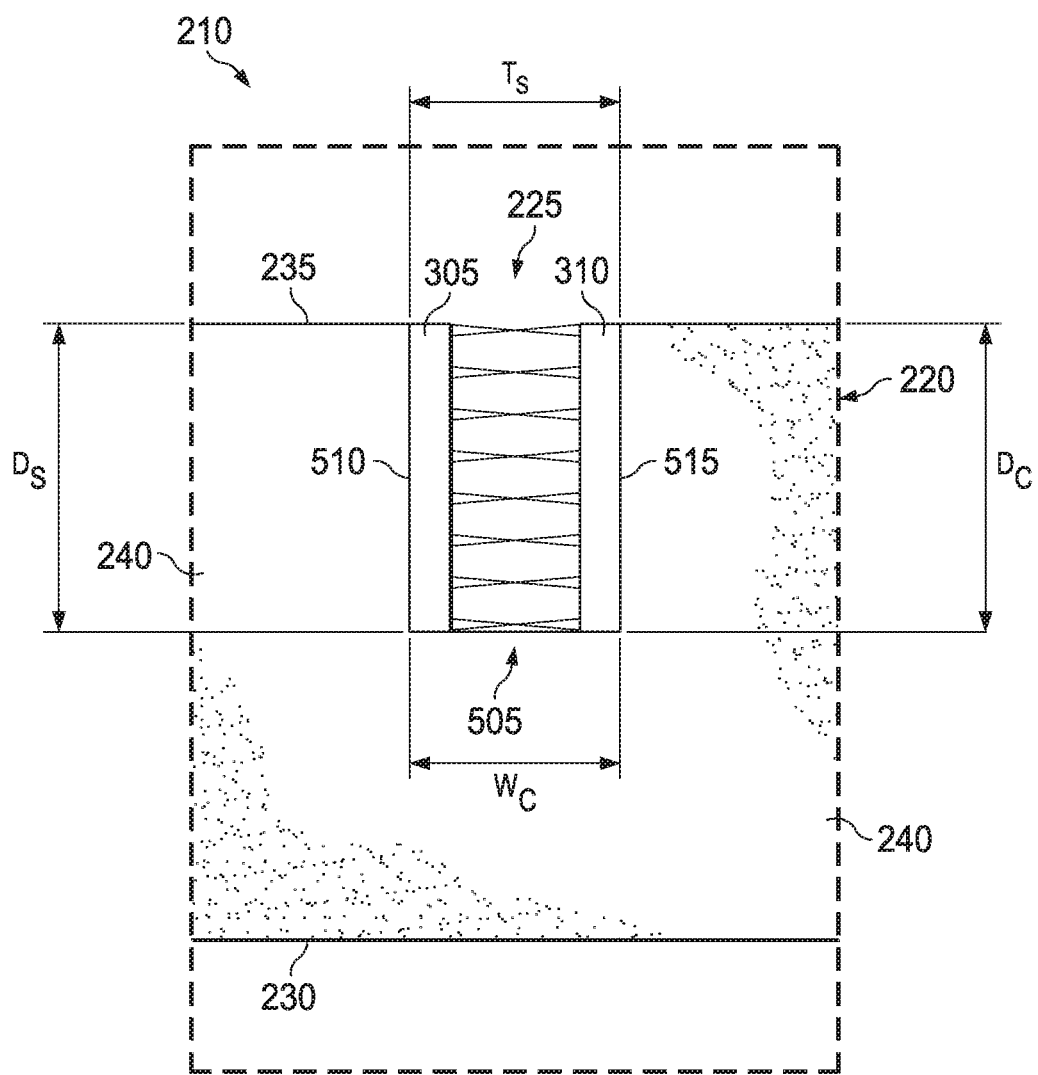
FIG. 5A is a side detail view of the layer of FIG. 5.

FIG. 5 and FIG. 5A illustrate another example of the manifold layer 210 that can be associated with some embodiments of the tissue interface 120 of FIG. 2. FIG. 5 is an exploded view of an example of the manifold layer 210. FIG. 5A is an assembled detail side view of the manifold layer 210. As shown in FIG. 5, in some embodiments, the manifold 220 may include one or more channels 505 extending into the manifold 220 on the second side 235. The channel 505 may include a first wall 510, a second wall 515 opposite the first wall 510 and a base wall 520 extending between the first wall 510 and the second wall 515. The first wall 510 and the second wall 515 may be perpendicular to the first side 230 and the second side 235 of the manifold 220. The first wall 510 and the second wall 515 may be parallel to the thickness $T_M$ of the manifold 220. The base wall 520 may be parallel to the first side 230 and the second side 235 of the manifold 220. The base wall 520 may be perpendicular to the thickness $T_M$ of the manifold 220.

The channel 505 may have a width $W_C$ measured between the first wall 510 and the second wall 515. The channel 505 may have a depth $D_C$ measured from the second side 235 of the manifold 220 to the base wall 520 of the channel 505. In some embodiments, the depth $D_C$ of the channel 505 may be less than the thickness $T_M$ of the manifold 220. For example, the depth $D_C$ of the channel 505 may be about 95% of the thickness $T_M$ of the manifold 220. In another example, the depth $D_C$ of the channel 505 may be about 75% of the thickness $T_M$ of the manifold 220. In yet another example, the depth $D_C$ of the channel 505 may be about 50% of the thickness $T_M$ of the manifold 220. In yet another example, the depth $D_C$ of the channel 505 may be about 25% of the thickness $T_M$ of the manifold 220. In some embodiments, the depth $D_C$ of the channel 505 may be equal to the thickness $T_M$ of the manifold 220. In embodiments where the depth $D_C$ of the channel 505 is equal to the thickness $T_M$ of the manifold 220, the channel 505 has no base wall 520 and forms a cut through the manifold 220. The thickness $T_S$ of the strip of spacer fabric 225 may be equal to the width $W_C$ of the channel 505. The strip of spacer fabric 225 may have a depth $D_S$, which, in some embodiments, may be equal to the depth $D_C$ of the channel 505.

As illustrated in FIG. 5A, the strip of spacer fabric 225 may be disposed in the channel 505, with the first layer 305 of the strip of spacer fabric 225 coupled to the first wall 510 of the channel 505 and the second layer 310 of the strip of spacer fabric 225 coupled to the second wall 515 of the channel 505. In some embodiments, the strip of spacer fabric 225 may be coextensive with the channel 505.

Figure 6:
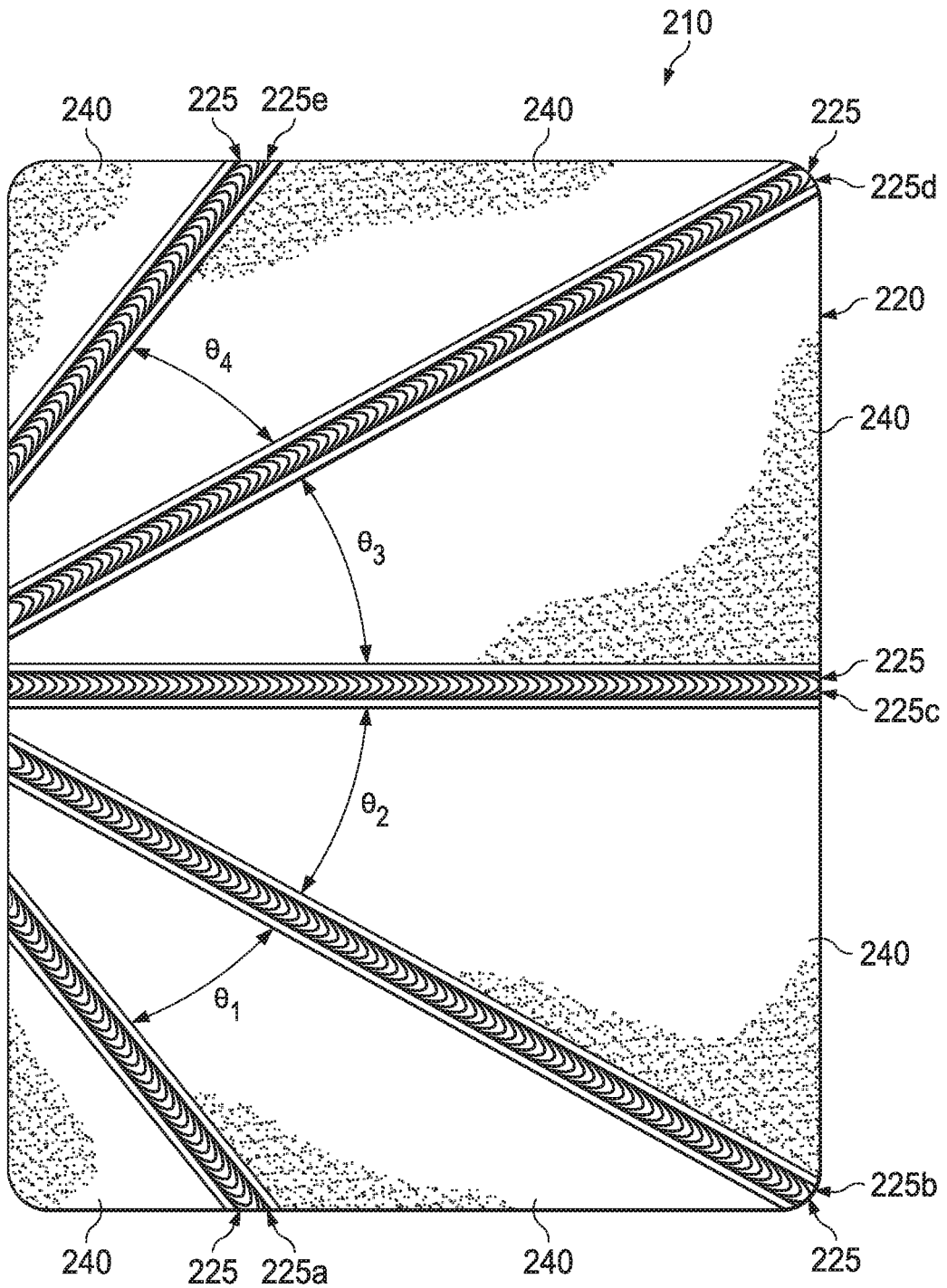
FIG. 6 is a top view of another example layer that can be associated with some embodiments of the tissue interface of FIG. 2.

FIG. 6 is a top view of another example of the manifold layer 210 that can be associated with some embodiments of the tissue interface 120 of FIG. 2. In some embodiments, the manifold layer 210 may include a plurality of strips of spacer fabric 225 wherein some or all of the strips of spacer fabric 225 are oriented at an angle with respect to one another. For example, as shown in FIG. 6, the manifold layer 210 may include a first strip of spacer fabric 225a, a second strip of spacer fabric 225b, a third strip of spacer fabric 225c, a fourth strip of spacer fabric 225d, and a fifth strip of spacer fabric 225e. The first strip of spacer fabric 225a may be at an angle $\theta_1$ with respect to the second strip of spacer fabric 225b, the second strip of spacer fabric 225b may be at an angle $\theta_2$ with respect to the third strip of spacer fabric 225c, the third strip of spacer fabric 225c may be at an angle $\theta_3$ with respect to the fourth strip of spacer fabric 225d, and the fourth strip of spacer fabric 225d may be at an angle $\theta_4$ with respect to the fifth strip of spacer fabric 225e. In some embodiments, some or all of the angles $\theta_1$, $\theta_2$, $\theta_3$, $\theta_4$, may be equal. In some embodiments, some or all of the angles $\theta_1$, $\theta_2$, $\theta_3$, $\theta_4$, may be different. In some embodiments, the first strip of spacer fabric 225a, the second strip of spacer fabric 225b, the third strip of spacer fabric 225c, the fourth strip of spacer fabric 225d, and the fifth strip of spacer fabric 225e may be identical to the strip of spacer fabric 225. In some embodiments, the first strip of spacer fabric 225a, the second strip of spacer fabric 225b, the third strip of spacer fabric 225c, the fourth strip of spacer fabric 225d, and the fifth strip of spacer fabric 225e may all have the same properties (e.g., the thickness of the first layer 305 and the second layer 310, the thickness $T_S$ of the strip of spacer fabric 225, and the filament material, the number of filaments, the weight of the filaments, and the denier per filament used to manufacture the first layer 305, the second layer 310, and the pile yarn 320). In some embodiments, one or more of the first strip of spacer fabric 225a, the second strip of spacer fabric 225b, the third strip of spacer fabric 225c, the fourth strip of spacer fabric 225d, and the fifth strip of spacer fabric 225e may have different properties. The strips of spacer fabric 225 may be oriented in the manifold 220 in any way as may be desired for therapy. For example, a non-parallel arrangement of the strips of spacer fabric 225 may allow for preferential contraction in certain areas of the tissue interface 120 to allow the tissue interface 120 to conform around or to specific geometries or anatomies.

Figure 7:
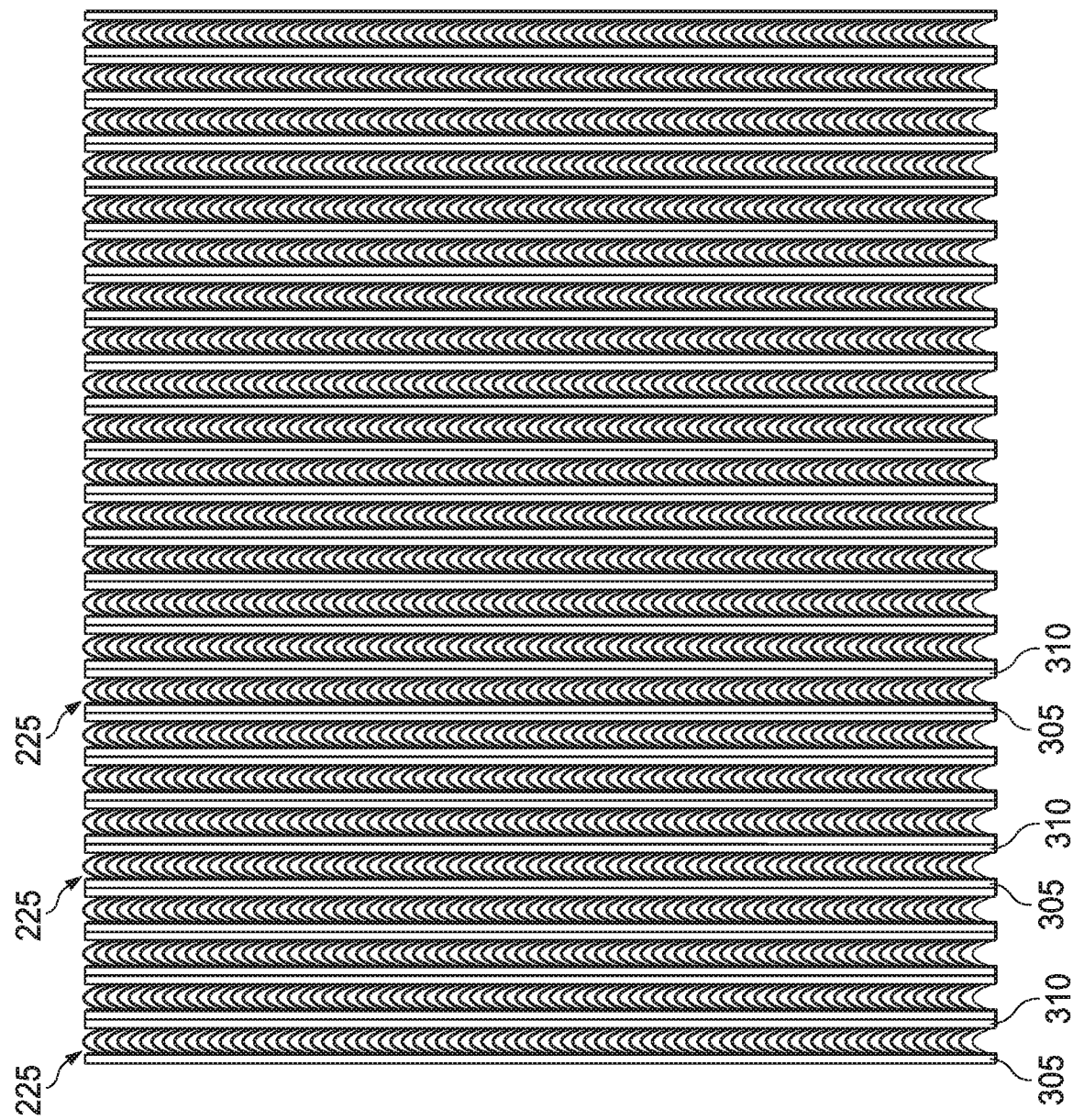
FIG. 7 is a top view of another example layer that can be associated with some embodiments of the tissue interface of FIG. 2.
Figure 8:
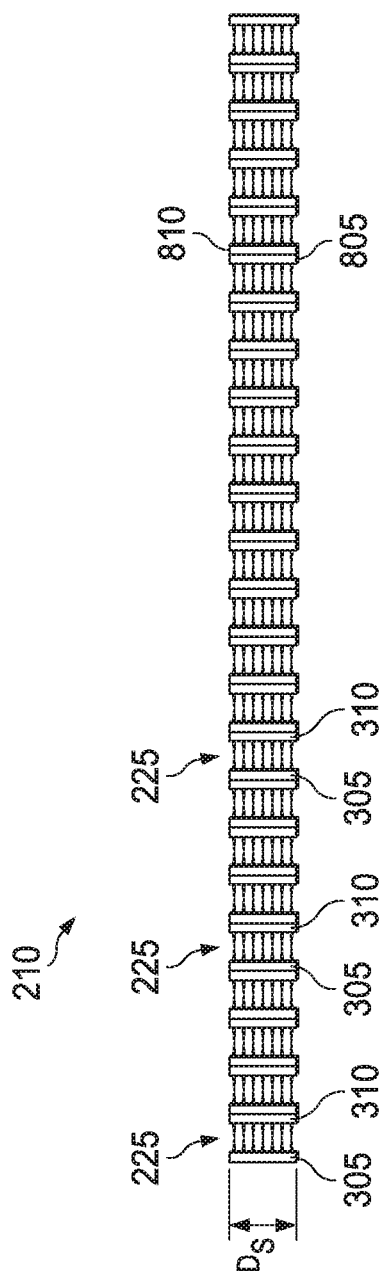
FIG. 8 is a side view of the layer of FIG. 7.

FIG. 7 and FIG. 8 illustrate another example of the manifold layer 210 that can be associated with some embodiments of the tissue interface 120 of FIG. 2. FIG. 7 is a top view of another example of the manifold layer 210. FIG. 8 is a side view of the manifold layer 210 of FIG. 7. As shown in FIG. 7, the manifold layer 210 may comprise or consist essentially of a plurality of strips of spacer fabric 225, wherein each strip of spacer fabric 225 is coupled directly to one or more adjacent strips of spacer fabric 225. For example, the first layer 305 of one strip of spacer fabric 225 may be coupled directly to the second layer 310 of an adjacent strip of spacer fabric 225. As shown in FIG. 8, the manifold layer 210 may have a first side 805 configured to face a tissue site, a second side 810 opposite the first side 805, and a thickness between the first side 805 and the second side 810, wherein the thickness is the depth $D_S$ of the spacer fabric 225. The first layer 305 and the second layer 310 of each strip of spacer fabric 225 may be oriented perpendicular to the first side 805 and the second side 810 of the manifold layer 210.

In some embodiments, one or more of the components of the dressing 110 may additionally be treated with an antimicrobial agent. For example, the manifold layer 210 may be coated with an antimicrobial agent. In some embodiments, the manifold layer 210 may comprise antimicrobial elements, such as fibers coated with an antimicrobial agent.

Additionally or alternatively, some embodiments of the contact layer 205 may be a polymer coated or mixed with an antimicrobial agent. Suitable antimicrobial agents may include, for example, metallic silver, PHMB, iodine or its complexes and mixes such as povidone iodine, copper metal compounds, chlorhexidine, or some combination of these materials.

Additionally or alternatively, one or more of the components may be coated with a mixture that may include citric acid and collagen, which can reduce bio-films and infections. For example, the manifold layer 210 may be coated with such a mixture.

The cover 125, the contact layer 205, the manifold layer 210, or various combinations may be assembled before application or in situ. For example, the contact layer 205 may be laminated to the manifold layer 210, and the cover 125 may be laminated to the manifold layer 210 opposite the contact layer 205 in some embodiments. In some embodiments, one or more layers of the tissue interface 120 may coextensive. For example, the contact layer 205 and the manifold layer 210 may be cut flush with the edge of the cover 125, exposing the edge of the manifold layer 210. In other embodiments, the contact layer 205 may overlap the edge of the manifold layer 210.

Figure 9:
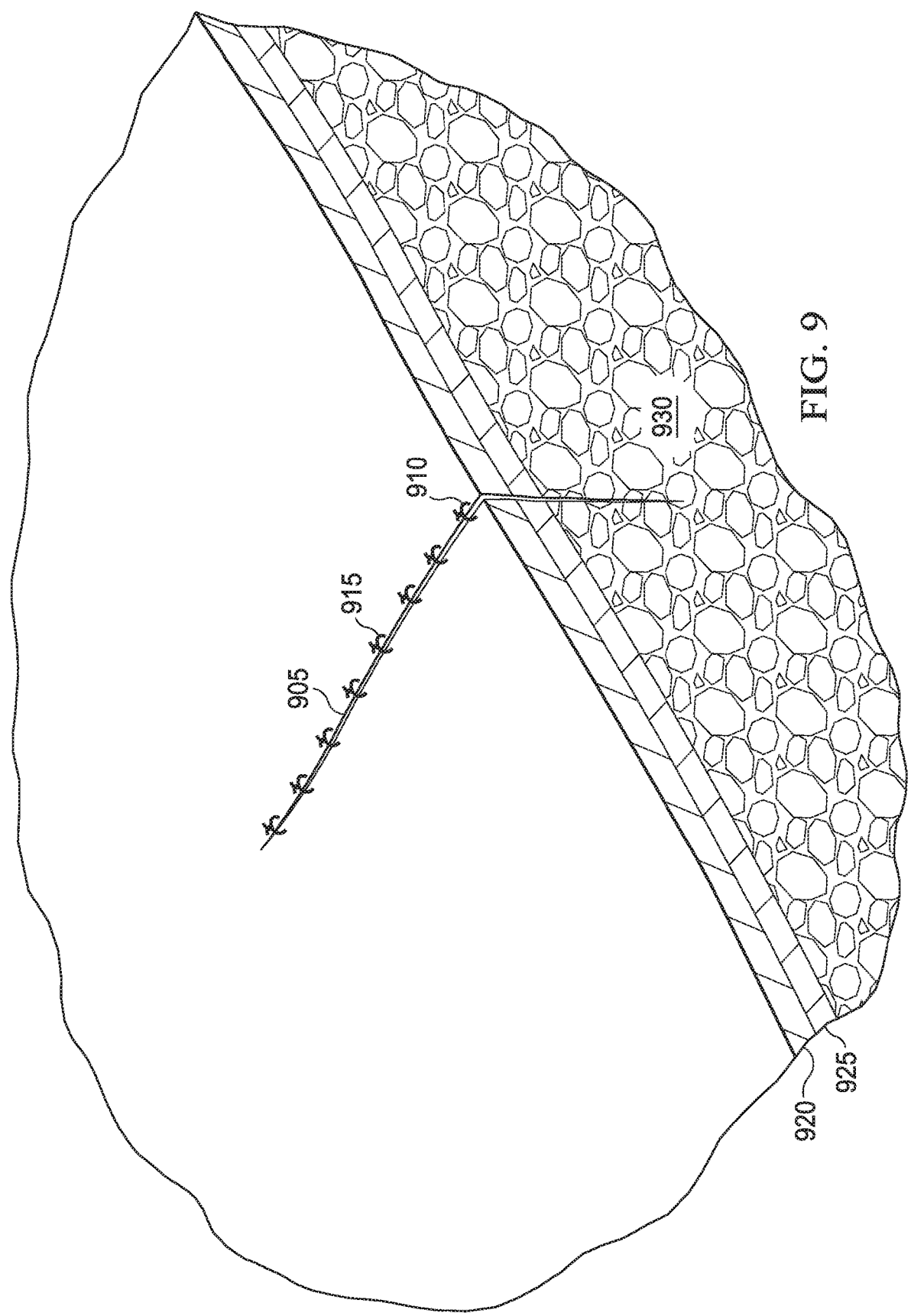
FIG. 9 is an isometric view, with a portion shown in cross-section, of a linear wound.
Figure 10:
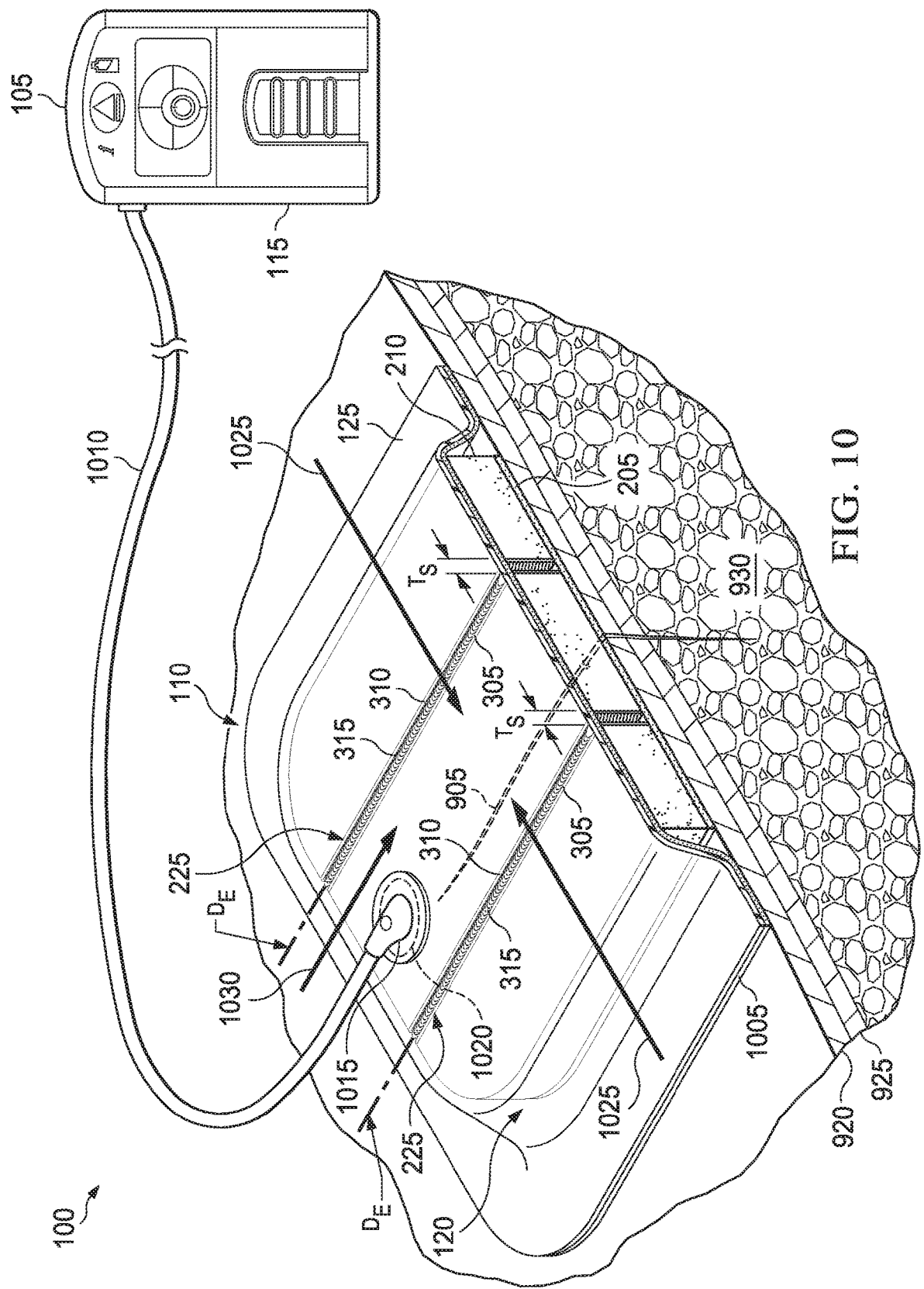
FIG. 10 is an isometric view, with a portion shown in cross-section, of a portion of an example embodiment of a therapy system being deployed over a linear wound.

Referring now primarily to FIG. 9 and FIG. 10, presented is another illustrative embodiment of a portion of the therapy system 100. FIG. 9 and FIG. 10 depict the therapy system 100 assembled in stages at a tissue site, such as a linear wound 905. In FIG. 9, a closure device 910, such as, for example, stitches 915, close the linear wound 905. Other closure devices 910, such as epoxy or staples may be utilized to close the linear wound 905. The linear wound 905 may include a portion through an epidermis 920, dermis 925, and subcutaneous tissue 930 of a patient.

Referring now to FIG. 10, after the linear wound 905 is closed or prepared as described above, the dressing 110 may be disposed proximate to the linear wound 905. The geometry and dimensions of the tissue interface 120, the cover 125, or both may vary to suit a particular application or anatomy. For example, the dressing 110 may be cut to size for a specific region or anatomical area, such as for amputations. The dressing 110 may be cut without losing pieces of the tissue interface 120 and without separation of the tissue interface 120.

The tissue interface 120 can be placed over, on, or otherwise proximate to the linear wound 905. In the example of FIG. 10, the contact layer 205 forms an outer surface of the dressing 110, and can be placed over the tissue site, including the linear wound 905 and epidermis 920. The contact layer 205 may be interposed between the manifold layer 210 and the tissue site, which can prevent direct contact between the manifold layer 210 and the linear wound 905 and epidermis 920. In some embodiments, the strips of spacer fabric 225 are oriented substantially parallel to the linear wound 905. For example, the extension direction $D_E$ of the one or more strips of spacer fabric 225 may be substantially parallel to the linear wound 905. In some embodiments, the tissue interface 120 may be placed on the tissue site, such that the linear wound 905 is between two strips of spacer fabric 225. In other embodiments, the tissue interface 120 may be placed on the tissue site, such that a strip of spacer fabric 225 overlays the linear wound 905.

In some examples, the dressing 110 may include one or more attachment devices. In some embodiments, one or more of the attachment devices may comprise or consist essentially of an adhesive 1005. In some examples the adhesive 1005 may be, for example, a medically-acceptable, pressure-sensitive adhesive that extends about a periphery, a portion, or an entire surface of each of the cover 125. In some embodiments, for example, the adhesive 1005 may be an acrylic adhesive having a coating weight between 25-65 grams per square meter (g.s.m.). Thicker adhesives, or combinations of adhesives, may be applied in some embodiments to improve the seal and reduce leaks. In some embodiments, such a layer of the adhesive 1005 may be continuous or discontinuous. Discontinuities in the adhesive 1005 may be provided by apertures or holes (not shown) in the adhesive 1005. The apertures or holes in the adhesive 1005 may be formed after application of the adhesive 1005 or by coating the adhesive 1005 in patterns on a carrier layer, such as, for example, a side of the cover 125. Apertures or holes in the adhesive 1005 may also be sized to enhance the MVTR of the adhesive 1005 in some example embodiments The adhesive 1005 can be disposed on a bottom side of the cover 125, and the adhesive 1005 may pressed onto the cover 125 and epidermis 920 (or other attachment surface) to fix the dressing 110 in position and to seal the tissue interface 120 over the patient. In some embodiments, the adhesive 1005 can be disposed only around edges of the cover 125.

FIG. 10 also illustrates one example of a fluid conductor 1010 and a dressing interface 1015. As shown in the example of FIG. 10, the fluid conductor 1010 may be a flexible tube, which can be fluidly coupled on one end to the dressing interface 1015. The dressing interface 1015 may be an elbow connector. In some examples, the tissue interface 120 can be applied to the tissue site before the cover 125 is applied over the tissue interface 120. The cover 125 may include an aperture 1020, or the aperture 1020 may be cut into the cover 125 before or after positioning the cover 125 over the tissue interface 120. The position of the aperture 1020 may be off-center or adjacent to an end or edge of the cover 125. In other examples, the aperture 1020 may be centrally disposed. The dressing interface 1015 can be placed over the aperture 1020 to provide a fluid path between the fluid conductor 1010 and the tissue interface 120. In other examples, the fluid conductor 1010 may be inserted directly through the cover 125 into the tissue interface 120.

If not already configured, the dressing interface 1015 may be disposed over the aperture 1020 and attached to the cover 125. The fluid conductor 1010 may be fluidly coupled to the dressing interface 1015 and to the negative-pressure source 105.

Negative pressure from the negative-pressure source 105 can be distributed through the fluid conductor 1010 and the dressing interface 1015 to the tissue interface 120. The tissue interface 120 may contract in response to the application of negative pressure. In some embodiments, the manifold layer 210 of the tissue interface 120 is configured to anisotropically contract. For example, under an applied negative pressure, the manifold layer 210 may contract more in a first direction 1025 than in a second direction 1030. The first direction 1025 may be perpendicular to the extension direction $D_E$ of the one or more strips of spacer fabric 225. The preferential contraction along the first direction 1025 by the manifold layer 210 acts to pull the epidermis 920 toward the linear wound 905 aiding in closing the linear wound 905.

The contact layer 205 can protect the epidermis 920 from irritation that could be caused by expansion, contraction, or other movement of the manifold layer 210. The contact layer 205 can also substantially reduce or prevent exposure of a tissue site to the manifold layer 210, which can inhibit growth of tissue into the manifold layer 210.

Although the strips of spacer fabric 225 are shown oriented parallel to the linear wound 905 in FIG. 10, it will be understood that in some embodiments, a tissue interface 120 may be applied to a tissue site wherein the one or more strips of spacer fabric 225 are oriented at an angle with respect to the linear wound 905. For example, in some embodiments, the tissue interface 120 may be tuned to preferentially contract along the extension direction $D_E$ of the one or more strips of spacer fabric 225 by modifying the material properties of the spacer fabric 225 and/or the manifold 220. In such embodiments, the strips of spacer fabric 225 may be oriented perpendicular to the linear wound 905 to aid in closure of the linear wound 905.

The systems, apparatuses, and methods described herein may provide significant advantages over prior dressings. For example, closure of the linear wound 905 may be promoted by orienting the strips of spacer fabric 225 parallel to the linear wound 905 when the dressing 110 is applied to the tissue site. Contraction of the manifold layer 210 more in a first direction, perpendicular to the linear wound 905, may be propagated by the manifold layer 210 and the cover 125 to the epidermis 920, dermis 925, and the subcutaneous tissue 930. The anisotropic contraction provided by the spacer fabric may reduce the chance for dehiscence and aids in drawing the edges of the linear wound 905 together. The dressing 110 may reduce healing complications and may promote healing at the tissue site.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for use in treating a tissue site with negative pressure, the dressing comprising:
   a manifold comprising an open cell foam, the manifold having a first side configured to face the tissue site, a second side opposite the first side, a thickness between the first side and the second side, a first portion, and a second portion; and
   a spacer fabric extending between the first portion and the second portion, the spacer fabric comprising:
   a first layer comprising a first knitted fabric having one or more multifilament yarns, the first layer coupled to the first portion, and the first layer forming a first face perpendicular to the first side of the manifold;
   a second layer comprising a second knitted fabric having one or more multifilament yarns, the second layer coupled to the second portion, and the second layer forming a second face perpendicular to the first side of the manifold; and
   a spacer layer comprising a plurality of pile yarns connecting the first layer and the second layer.

2. The dressing of claim 1, wherein the first portion and the second portion of the manifold are drawn toward one another in response to an application of negative pressure to the dressing.

3. The dressing of claim 1, wherein the first layer and the second layer are configured to be drawn toward one another under an application of negative pressure.

4. The dressing of claim 1, wherein the plurality of pile yarns are interknitted with the first layer and the second layer.

5. The dressing of claim 1, wherein the spacer fabric extends into the manifold on the second side and has a depth measured from the second side, wherein the depth is less than or equal to the thickness of the manifold.

6. The dressing of claim 1, wherein:
   the spacer fabric extends in an extension direction across the manifold; and
   the dressing is configured to anisotropically contract such that the dressing is configured to contract more in a first direction than in a second direction, wherein the first direction is perpendicular to the extension direction of the spacer fabric.

7. The dressing of claim 1, wherein the spacer fabric is a first spacer fabric and the dressing further comprises a second spacer fabric.

8. The dressing of claim 7, wherein the second spacer fabric is parallel to the first spacer fabric.

9. The dressing of claim 7, wherein the second spacer fabric is at an angle relative to the first spacer fabric.

10. The dressing of claim 1, further comprising a contact layer coupled to the first side of the manifold.

11. A dressing for treating a tissue site with negative pressure, the dressing comprising:
    a manifold comprising an open cell foam, the manifold having a first side configured to face the tissue site, a second side opposite the first side, and a thickness between the first side and the second side;
    a channel extending into the manifold on the second side, the channel having a first wall, a second wall opposite the first wall, a base wall extending between the first wall and the second wall, and a depth measured from the second side of the manifold to the base wall of the channel, the depth of the channel less than the thickness of the manifold, wherein the first wall and the second wall are perpendicular to the first side of the manifold and the base wall is parallel to the first side of the manifold; and
    a spacer fabric disposed in the channel, the spacer fabric comprising:
    a first fabric layer coupled to the first wall of the channel, the first fabric layer having a first face perpendicular to the first side of the manifold;
    a second fabric layer coupled to the second wall of the channel, the second fabric layer having a second face perpendicular to the first side of the manifold; and a spacer layer coupled to and extending between the first fabric layer and the second fabric layer;

wherein a portion of each of the first fabric layer and the second fabric layer are at the second side of the manifold.

12. The dressing of claim 11, wherein the first fabric layer and the second fabric layer are configured to be drawn toward one another under an application of negative pressure.

13. The dressing of claim 11, wherein the first fabric layer comprises multifilament yarns and the second fabric layer comprises multifilament yarns.

14. The dressing of claim 11, wherein the spacer layer comprises a plurality of pile yarns connecting the first fabric layer and the second fabric layer.

15. The dressing of claim 11, wherein the spacer fabric extends in an extension direction across the manifold, and wherein the spacer fabric is configured to resist contraction parallel to the extension direction.

16. A dressing for treating a tissue site with negative pressure, the dressing comprising:

a tissue interface having a first side configured to face the tissue site, a second side opposite the first side, and a thickness between the first side and the second side, the tissue interface comprising:

two or more strips of spacer fabric, each of the two or more strips of spacer fabric having:

a first fabric layer having a first face, the first face perpendicular to the first side of the tissue interface;

a second fabric layer having a second face, the second face perpendicular to the first side of the tissue interface; and a spacer layer comprising one or more yarns interknitted with the first fabric layer and the second fabric layer; and a manifold between each strip of spacer fabric, the manifold and the two or more strips of spacer fabric coupled to one another.

17. The dressing of claim 16, wherein the first fabric layer and the second fabric layer are configured to be drawn toward one another under an application of negative pressure.

18. The dressing of claim 16, wherein the one or more yarns comprises monofilaments.

19. The dressing of claim 1, wherein the first layer and the second layer of the spacer fabric are coupled to the manifold with one or more of glue, hot melt adhesive, and welds.

20. The dressing of claim 1, wherein the manifold has a width and a length, the spacer fabric extends in an extension direction across the manifold, and the spacer fabric is configured to resist contraction of the manifold parallel to the extension direction when negative pressure is applied to the dressing.

* * * * *